United States Patent [19]

Stack et al.

[11] Patent Number: 5,166,367

[45] Date of Patent: Nov. 24, 1992

[54] ANTIPSYCHOTIC BENZODIOXAN DERIVATIVES

[75] Inventors: Gary P. Stack, Ambler; Terrance H. Andree, Doylestown, both of Pa.; Noreen T. Scherer, Plainsboro, N.J.

[73] Assignee: American Home Products Corporation, New York, N.Y.

[21] Appl. No.: 719,882

[22] Filed: Jun. 21, 1991

[51] Int. Cl.$^5$ .................. C07D 311/10; C07D 311/20
[52] U.S. Cl. .................. 549/289; 549/378; 549/379; 549/380
[58] Field of Search ................ 549/289, 378, 379, 380

[56] References Cited

U.S. PATENT DOCUMENTS

| Re. 30,739 | 9/1981 | Gardner | 549/289 |
|---|---|---|---|
| 3,663,570 | 5/1972 | Sato et al. | 549/289 |
| 3,810,898 | 5/1974 | Witte et al. | 549/289 |
| 5,073,563 | 12/1991 | Frickel et al. | 549/289 |

FOREIGN PATENT DOCUMENTS

| 170213 | 2/1986 | European Pat. Off. |
| 175541 | 3/1986 | European Pat. Off. |
| 236930 | 9/1987 | European Pat. Off. |
| 2477542 | 9/1981 | France . |
| 57-142972 | 9/1982 | Japan . |
| 58-219114 | 12/1983 | Japan . |
| 6407012 | 12/1964 | Netherlands . |

*Primary Examiner*—C. Warren Ivy
*Assistant Examiner*—Ba K. Trinh
*Attorney, Agent, or Firm*—Richard K. Jackson

[57] ABSTRACT

A compound of the formula:

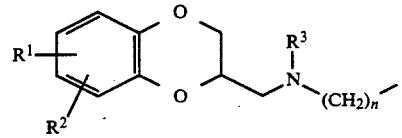

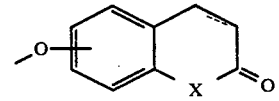

wherein the dotted line represents optional unsaturation; $R^1$ and $R^2$ are, independently, hydrogen, alkyl, alkoxy, aralkoxy, alkanoyloxy, hydroxy, halo, amino, mono- or dialkylamino, alkanamido or sulfonamido or $R^1$ and $R^2$ together are methylenedioxy, ethylenedioxy or propylenedioxy; $R^3$ is hydrogen or alkyl; n is one of the integers 2, 3 or 4; X is O or $NR^4$, in which $R^4$ is hydrogen or alkyl; or a pharmaceutically acceptable salt thereof, are antipsychotic agents.

17 Claims, No Drawings

ANTIPSYCHOTIC BENZODIOXAN DERIVATIVES

BACKGROUND OF THE INVENTION

European Patent Application EP 175,541 discloses a series of aminoalkoxybenzopyranones (I), useful as antipsychotic and anxiolytic agents, in which $R^1$ is aryl or heteroaryl piperazinyl or piperidinyl, R is hydrogen, lower alkyl, trifluoromethyl, or lower alkoxy, and n is an integer from 2 to 5.

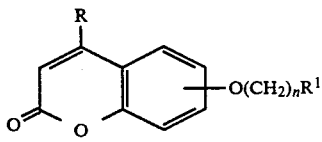

Japanese Kokai Tokkyo Koho JP 57,142,972 and Fr. Demande FR 2,477,542 claim compounds of formula (II) as antihistaminic, anti-aggressive, and adrenaline antagonistic agents, useful as central nervous system agents. R is H, alkyl, phenylalkyl, alkenyl, alkynyl; Z is N-phenylimino, (un)substituted benzylidene; n is 0 or 1; $Z^1$ is alkylene; and $Z^2$ is CO, CH(OH), (un)substituted vinylene or ethylene.

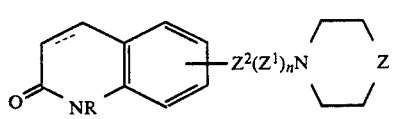

European Patent Application EP 170,213 discloses a series of glutarimide derivatives of benzodioxan methanamine as antianxiety and antihypertensive agents. Fozard et. al. Br. J. Pharmacol. 90,273P (1987) disclose 8-[4-(1,4-benzodioxan-2-ylmethylamino)butyl]-8-azaspiro[4.5]decane-7,9-dione (MDL 72832) as a selective and stereospecific [(−)-MDL 72832 binds 32 times as much as the dextrorotary isomer at the 5-$HT_{1A}$ receptor site] ligand for 5-$HT_{1A}$ receptors.

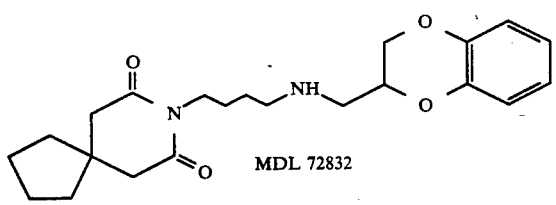

MDL 72832

European Patent EP 236,930 discloses a series of 2-substituted-alkyl-1,2-benzisothiazole-3-one 1,1-dioxide derivatives useful as anxiolytic and antihypertensive agents. Specifically claimed is 2-(4-(2,3-dihydro-1,4-benzodiox-2-yl)methylamino)butyl)-1,2-benzisothiazol-3(2H)-one 1,1-dioxide.

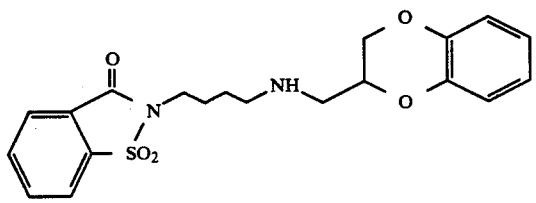

Netherlands 6,407,012 claims compounds of general formula (III), in which R, R1 and R2 are H, halogen, (1–6 C) alkyl, or (1–6 C) O-alkyl and n is an integer 2–6, as calming, hypnotic and hypotensive agents. Japanese Kokai Tokkyo Koho JP 58,219,114 claims similar compounds in which the two oxygen substituents in the phenoxy moiety are joined by a methylene, ethylene, or propylene bridge.

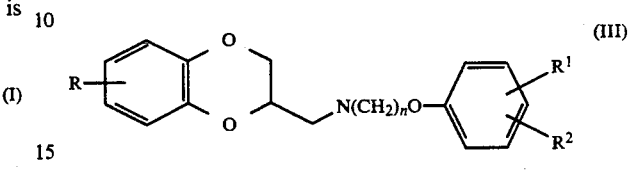

DESCRIPTION OF THE INVENTION

In accordance with this invention, there is provided a group of novel antipsychotic agents of the formula:

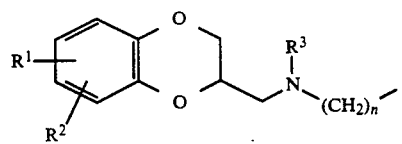

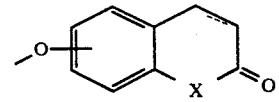

wherein
the dotted line represents optional unsaturation;
$R^1$ and $R^2$ are, independently, hydrogen, alkyl of 1 to 6 carbon atoms, alkoxy of 1 to 6 carbon atoms, aralkoxy of 7 to 12 carbon atoms, alkanoyloxy of 2 to 6 carbon atoms, hydroxy, halo, amino, mono- or dialkylamino in which each alkyl group has 1 to 6 carbon atoms, alkanamido of 2 to 6 carbon atoms or sulfonamido or $R^1$ and $R^2$ together are methylenedioxy, ethylenedioxy or propylenedioxy;
$R^3$ is hydrogen or alkyl of 1 to 6 carbon atoms;
n is one of the integers 2, 3 or 4;
X is O or $NR^4$, in which $R^4$ is hydrogen or alkyl of 1 to 6 carbon atoms;
or a pharmaceutically acceptable salt thereof.

Of these compounds, the preferred members are those in which $R^1$ and $R^2$ are, independently, fluoro, hydrogen, hydroxy, alkoxy of 1 to 6 carbon atoms or alkanoyloxy of 2 to 6 carbon atoms, or together form a methylenedioxy, ethylenedioxy or propylenedioxy ring; n, X, and $R^3$ are defined as above and the connection from the oxygen to the coumarin (X=O) or carbostyril (X=$NR^4$) moiety is in the 7 position.

Most preferred are those members in which $R^1$ and $R^2$ are located in the 6 and 7 positions of the benzodioxan moiety and are defined as fluoro, hydrogen, hydroxy, alkoxy of 1 to 6 carbon atoms or alkanoyloxy of 2 to 6 carbon atoms, or together form alkylenedioxy of 1 to 3 carbon atoms; $R^3$ is hydrogen or alkyl of 1 to 6 carbon atoms; n is 3; X is oxygen, the connection from the oxygen to the coumarin moiety is at C-7, the dashed line is replaced with a solid line to represent unsaturation, and the configuration of the benzodioxan methanamine is S.

The pharmaceutically acceptable salts are those derived from such organic and inorganic acids as: acetic, lactic, citric, tartaric, succinic, maleic, malonic, hydrochloric, hydrobromic, phosphoric, nitric, sulfuric, methanesulfonic, and similarly known acceptable acids.

The compounds of this invention are prepared by conventional methods. For example, the appropriately substituted benzodioxan methanamine is combined with a suitable alkyl halide in the presence of an acid scavenger such as diisopropylethylamine in a solvent such as dimethylformamide and heated at 80°-100° C. for 24 hours (1). Alternatively, a benzodioxan methylhalide or tosylate may be combined with the appropriate aminoalkoxycoumarin or aminoalkoxycarbostyril under similar conditions and heated for an extended period (2). The amine component may also be combined with a suitably substituted aldehyde and a reducing agent such as sodium cyanoborohydride (3), or with the appropriate acid chloride followed by reduction by an agent such as borane/THF (4).

The haloalkoxycoumarins and carbostyrils appropriate for the above procedure are known compounds; the aminoalkoxycoumarins and carbostyrils may be readily prepared from them as shown above. The aldehydes and carboxylic acid chlorides appropriate to (3) and (4) may be readily prepared by one schooled in the art. The benzodioxan methanamines themselves are known compounds, or they can readily be derived from the appropriate salicylaldehyde by the procedure illustrated below. The benzodioxan methanamines may be resolved into their enantiomers by conventional methods or, preferably, they may be prepared directly by substitution of (2R)-(−)-glycidyl 3-nitrobenzenesulfonate (for the S benzodioxan methanamine) or (2S)-(+)-glycidyl 3-nitrobenzenesulfonate (for the R enantiomer) in place of epichlorohydrin in the procedure below. Throughtout this application, the name of a product of this invention, where the absolute configuration of the benzodioxan methanamine is not indicated, is intended to embrace the R and S isomers, as well as a mixture of the R and S isomers.

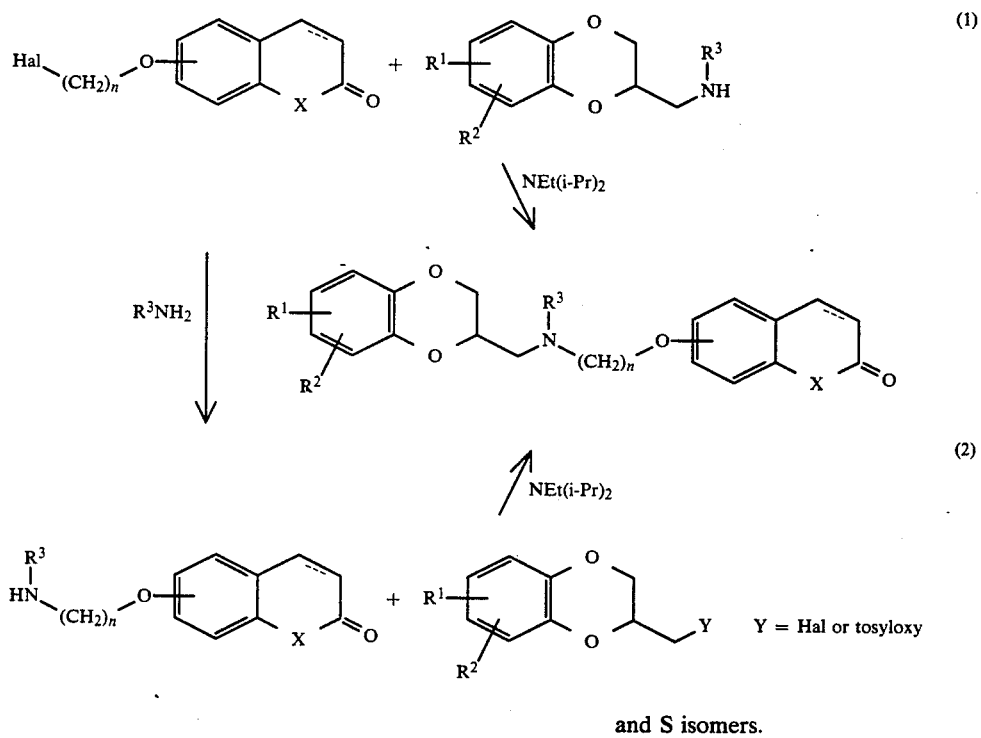

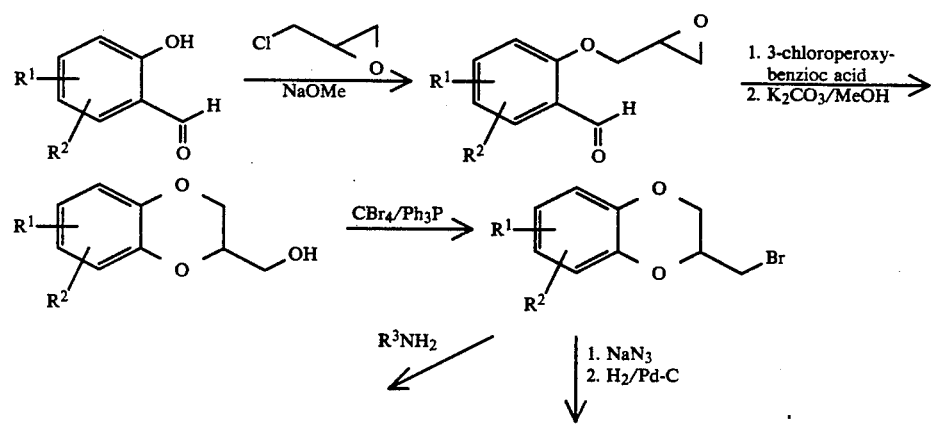

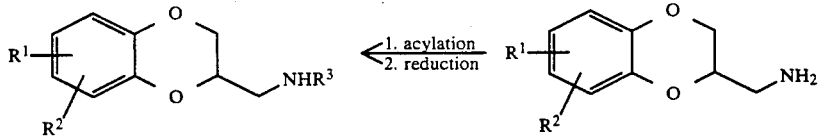

-continued

The compounds of this invention are dopamine autoreceptor agonists; that is, they serve to modulate the synthesis and release of the neurotransmitter dopamine. They are thus useful for treatment of disorders of the dopaminergic system, such as schizophrenia, Parkinson's disease and Tourette's syndrome. Such agents are partial agonists at the postsynaptic dopamine $D_2$ receptor and are thereby useful in the treatment of drug addiction. Certain of the compounds of the invention also possess high affinity for serotonin $5\text{-}HT_{1A}$ receptors and consequently, like the serotonergic agent buspirone, they are useful as antidepressant and anxiolytic agents for the treatment of a variety of central nervous system disorders such as depression, anxiety, sleep and eating disorders, sexual dysfunction, and related problems.

The effect of the compounds of the invention on the synthesis of dopamine was established by the method of Walters and Roth, Naunyn-Schmiedeberg's Arch. Pharmacol. 296:5-14, 1976, in which rats (male, Sprague-Dawley, Charles River, 200-350 g) were administered vehicle or test drug ten minutes prior to the administration of gamma butyrolactone (GBL; 750 mg/kg, ip to inhibit dopaminergic impulse flow) and 20 minutes prior to NSD-1015 (100 mg/kg, ip to prevent the conversion of dopa to dopamine). Thirty minutes after NSD-1015 all rats were humanely euthenized and the nucleus accumbens and the striatum were removed for analysis. Following perchloric acid extraction of the tissue, the extracts were placed over alumina columns to collect and concentrate dopa and other catechols. This eluate was then subjected to HPLC analysis using electrochemical detection to quantify the levels of dopa present. Dopamine autoreceptor agonists, under the conditions used above, inhibit dopa accumulation. The results of this testing with compounds representative of this invention are reported below as % inhibition of dopa accumulation at 10 mg/kg, sc in either limbic (L) or striatal (S) brain tissue.

The antipsychotic activity of the compounds of the invention was further established by a determination of the compounds' ability to reduce mouse locomotor activity according to the method of Martin and Bendensky, J. Pharmacol. Exp. Therap. 229:706–711, 1984, in which mice (male, CF-1, Charles River, 20–30 g) were injected with vehicle or various doses of each drug and locomotor activity was measured for 30 minutes using automated infrared activity monitors (Omnitech-8×8 inch open field) located in a darkened room. $ED_{50}$'s were calculated from the horizontal activity counts collected from 10 to 20 minutes after dosing using a nonlinear regression analysis with inverse prediction. The results of this test with compounds of the invention are reported below.

Affinity for the dopamine $D_2$ receptor was established by the standard experimental test procedure of Fields, et al., Brain Res., 136, 578 (1977) and Yamamura et al., eds., Neurotransmitter Receptor Binding, Raven Press, N.Y. (1978) wherein homogenized limbic brain tissue is incubated with $^3$H-spiroperidol and various concentrations of test compound, filtered and washed and shaken with Hydrofluor scintillation cocktail (National Diagnostics) and counted in a Packard 460 CD scintillation counter. The results of this testing with compounds representative of this invention are also given below.

Affinity for the serotonin $5\text{-}HT_{1A}$ receptor was established by testing the claimed compound's ability to displace [$^3$H] 8-OHDPAT (dipropylaminotetralin) from the $5\text{-}HT_{1A}$ serotonin receptor following the procedure of Hall et al., J. Neurochem. 44, 1685 (1985). This procedure is employed to analogize this property of the claimed compounds with that of buspirone, which is a standard for anxiolytic activity, and, like the compounds of this invention, displays potent affinity for the $5\text{-}HT_{1A}$ serotonin receptor subtype. The anxiolytic activity of buspirone is believed to be, at least partially, due to its $5\text{-}HT_{1A}$ receptor affinity (Vander Maclen et al., Eur. J. Pharmacol. 1986, 129 (1–2) 133–130).

The results of the standard experimental test procedures described in the preceding four paragraphs were as follows:

| Compound | Dopa Accumulation (% inhib. @ 10 mg/kg, sc | Hypolocomotion (ED$_{50}$ mg/kg, ip) | Receptor Affinities (IC$_{50}$ (nM) or % @ () μM) | |
|---|---|---|---|---|
| | | | D$_2$ | 5-HT$_{1A}$ |
| Example 1 | 39 (L)/1 (S) | 0.58 | 112 nM | 0.5 nM |
| Example 2 | −12 (L) | | | |
| Example 4 | 20 (L) | | | |
| Example 5 | 60 (L)/18 (S) | 1.62/2.04 | 337/730 nM | 112 nM |
| Example 6 | 76 (L)/73 (S) | 0.19 | 100% (1.0) | 6 nM |
| Example 7 | 1.5 (L)/51.3 (S) | | | |
| Example 8 | 50 (L) | 3.5 | 104 nM | |
| Example 9 | 21.7 (L) | | 66% (1.0) | |
| Example 10 | 24.0 | | | |
| Example 11 | 37.7 (L) | | | 78% (0.1) |
| Example 12 | 61.6 (L) | 1.6 | | 81% (0.1) |
| Example 13 | 6.9 (L)/18 (L) | | | |
| Example 14 | 19.5 | | | |
| Example 15 | 9.2 | | | 23% (0.1) |
| Example 19 | 23 (L) | | | |
| Example 20 | 45 (L) | | | |

Hence, the compounds of this invention have a pronounced effect on the synthesis of the neurotransmitter dopamine and thus are useful in the treatment of dopaminergic disorders such as schizophrenia, Parkinson's disease, Tourette's syndrome and drug addiction. Certain compounds of this invention also demonstrated high affinity for both the serotonin 5-HT$_{1A}$ and dopamine D$_2$ receptor subtypes, and are therefore useful in the treatment of multi-CNS disorders amenable to treatment with antipsychotic, antidepressant and anxiolytic agents.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis, state of anxiety or CNS dysfunction must be subjectively determined by the attending physician. The variables involved include the specific psychosis, state of anxiety or CNS related problems and the size, age and response pattern of the patient.

The following examples illustrate the production of representative compounds of this invention.

EXAMPLE 1

7-[3-[[(2,3-Dihydro-1,4-benzodioxin-2-yl)methyl]amino]propoxy]-2H-1-benzopyran-2-one 2,3-Dihydro-1,4-benzodioxin-2-methanamine (1.7 g, 10 mmole), 7-(3-chloropropoxy)coumarin (2.4 g, 10 mmole), diisopropylethylamine (1.3 g, 10 mmole) and sodium iodide (5.0 g, 33 mmole) were combined in 100 ml of N-methylpyrrolidinone and heated at 80° C. for 24 hours under a nitrogen atmosphere. The solvent was then removed and replaced with 300 ml of dichloromethane. The mixture was washed with an equal volume of saturated aqueous sodium bicarbonate, with saturated aqueous sodium chloride, dried over sodium sulfate, filtered, and concentrated in vacuum. The residue was column chromatographed on 100 g of silica gel using chloroform as eluant. The product-containing fractions (Rf=0.15 on silica gel tlc with 1% methanol/chloroform) were combined and concentrated in vacuum and the residue crystallized from isopropanol with the addition of 4N isopropanolic HCl to give 1.1 g of title compound as a tan solid, monohydrochloride, m.p. 213°-215° C.

Elemental Analysis for: $C_{21}H_{21}NO_5.HCl$: Calcd: C, 62.45; H, 5.49; N, 3.47; Found: C, 62.67; H, 5.65; N, 3.37

EXAMPLE 2

7-[3-[[(2,3-Dihydro-5-methoxy-1,4-benzodioxin-2-yl)methyl]amino]propoxy]-2H-1-benzopyran-2-one 2,3-Dihydro-5-methoxy-1,4-benzodioxin-2-methanamine (1.29 g, 6.61 mmole), 7-(3-chloropropoxy)coumarin (1.59 g, 6.7 mmole), diisopropylethylamine (2.5 ml, 14.35 mmole) and sodium iodide (4.96 g, 33.1 mmole) were combined in 75 ml of DMF and heated at 80°-100° C. for 3 days under a nitrogen atmosphere. The solvent was then removed and replaced with dichloromethane. The mixture was washed with an equal volume of saturated aqueous sodium bicarbonate, with saturated aqueous sodium chloride, dried over magnesium sulfate, filtered, and concentrated in vacuum. The residue was column chromatographed on silica gel using 30% ethyl acetate/dichloromethane as eluant. The product-containing fractions (Rf=0.25 on silica gel tlc with 2.5% methanol/dichloromethane) were combined and concentrated in vacuum and the residue (0.68 g) redissolved in dichloromethane and boiled on a hot plate, the dichloromethane gradually being replaced with isopropanol. 2N HCl/isopropanol (4 ml) was added and the title compound was collected by filtration and dried in vacuum at 80° C. The procedure yielded 0.64 g of white solid, monohydrochloride, m.p. 202°-204° C.

Elemental Analysis for: $C_{22}H_{23}NO_6.HCl$: Calcd: C, 60.91; H, 5.57; N, 3.23; Found: C, 61.04; H, 5.46; N, 3.13

EXAMPLE 3

7-[3-[[(2,3-Dihydro-7-phenylmethoxy-1,4-benzodioxin-2-yl)methyl]amino]propoxy]-2H-1-benzopyran-2-one 2,3-Dihydro-7-benzyloxy-1,4-benzodioxin-2-methanamine (1.47 g, 5.42 mmole), 7-(3-chloropropoxy)coumarin (1.30 g, 5.45 mmole), diisopropylethylamine (4.0 ml, 23 mmole) and sodium iodide (4.17 g, 28 mmole) were combined in 150 ml of DMF and heated at 80°-100° C. for 2 days under a nitrogen atmosphere. The solvent was then removed and replaced with dichloromethane. The mixture was washed with an equal volume of saturated aqueous sodium bicarbonate, with saturated aqueous sodium chloride, dried over magnesium sulfate, filtered, and concentrated in vacuum. The residue was column chromatographed on silica gel using first dichloromethane, then 0.5% methanol/dichloromethane, and finally 1% methanol/dichloromethane as eluant. The fractions containing material with Rf=0.26 on silica gel tlc (2.5% methanol/chloroform) were combined and concentrated in vacuum and the residue crystallized from 50 ml of isopropanol with the addition of 4.0 ml of 4N isopropanolic HCl to give 0.66 g of title compound as an off-white solid, monohydrochloride, m.p. 179°-181° C.

Elemental Analysis for: $C_{28}H_{27}NO_6 \cdot HCl$: Calcd: C, 65.94; H, 5.53; N, 2.75; Found: C, 65.60; H, 5.19; N, 2.91

EXAMPLE 4

7-[3-[[(2,3-Dihydro-6-phenylmethoxy-1,4-benzodioxin-2-yl)methyl]amino]propoxy]-2H-1-benzopyran-2-one 2,3-Dihydro-6-benzyloxy-1,4-benzodioxin-2-methanamine (2.4 g, 8.85 mmole), 7-(3-chloropropoxy)-coumarin (2.15 g, 9.0 mmole), diisopropylethylamine (7.0 ml, 40.2 mmole) and sodium iodide (1.35 g, 9.0 mmole) were combined in 200 ml of DMF and heated at 108° C. for 2 days under a nitrogen atmosphere. The solvent was then removed and replaced with dichloromethane. The mixture was washed with an equal volume of water dried over magnesium sulfate, filtered, and concentrated in vacuum. The residue was column chromatographed on silica gel using 1% methanol/dichloromethane as eluant. The product-containing fractions (Rf=0.27 on silica gel tlc with 2.5% methanol/dichloromethane) were combined and concentrated in vacuum and the residue redissolved in dichloromethane and boiled on a hot plate, the solvent gradually being replaced with isopropanol. Upon addition of 6 ml of 4N HCl/isopropanol and cooling, 1.22 g of the title compound, m.p. 184°-187° C., precipitated as a beige solid, monohydrochloride.

Elemental Analysis for: $C_{28}H_{27}NO_6 \cdot HCl$: Calcd: C, 65.94; H, 5.53; N, 2.75; Found: C, 65.74; H, 5.49; N, 2.96

EXAMPLE 5

7-[3-[[(2,3-Dihydro-6-hydroxy-1,4-benzodioxin-2-yl)methyl]amino]propoxy]-2H-1-benzopyran-2-one 7-[3-[[(2,3-Dihydro-6-phenylmethoxy-1,4-benzodioxin-2-yl)methyl]amino]propoxy]-2H-1-benzopyran-2-one hydrochloride (0.82 g, 1.6 mmole), prepared in Example 4 above, was dissolved in a mixture of 150 ml of water and 10 ml of methanol, 300 mg of 5% palladium on carbon added, and the mixture hydrogenated at 25 psi on a Parr apparatus for 4.5 hours. It was then filtered through celite and concentrated to dryness in vacuum. The residue was redissolved in methanol and boiled on a hot plate, the methanol being gradually replaced with isopropanol, and an additional 2.8 ml of 4N HCl/isopropanol was added. Upon cooling 0.37 g of the title compound, m.p. 244° C. (d), precipitated as a white solid, monohydrochloride.

Elemental Analysis for: $C_{21}H_{21}NO_6 \cdot HCl$: Calcd: C, 60.07; H, 5.28; N, 3.34; Found: C, 59.77; H, 5.38; N, 3.11

EXAMPLE 6

7-[3-[[(2,3-Dihydro-7-hydroxy-1,4-benzodioxin-2-yl)methyl]amino]propoxy]-2H-1-benzopyran-2-one.

2,3-Dihydro-7-hydroxy-1,4-benzodioxin-2-methanamine (3.00 g, 16.6 mmole), 7-(3-chloropropoxy)coumarin (2.95 g, 12.4 mmole), diisopropylethylamine (8.0 ml, 46.0 mmole) and sodium iodide (2.58 g, 17.2 mmole) were combined in 150 ml of DMF and heated at 80°-100° C. for 2 days under a nitrogen atmosphere. The solvent was then removed and replaced with dichloromethane. The mixture was washed with an equal volume of saturated aqueous sodium bicarbonate, with saturated aqueous sodium chloride, dried over magnesium sulfate, filtered, and concentrated in vacuum. The residue was column chromatographed on silica gel using first dichloromethane and then 0.25% methanol/dichloromethane as eluant. The product-containing fractions were combined and concentrated in vacuum and the pure free base (1.0 g, an additional 2.0 g were obtained of lower purity) redissolved in methanol and boiled on a hot plate, the methanol gradually being replaced with isopropanol. 4N HCl/IPA was added and the title compound was collected by filtration and dried in vacuum at 80° C. The procedure yielded 0.76 g of beige solid, monohydrochloride, m.p. 252° C. (d).

Elemental Analysis for: $C_{21}H_{21}NO_6 \cdot HCl$: Calcd: C, 60.07; H, 5.28; N, 3.34; Found: C, 59.73; H, 5.59; N, 3.31

EXAMPLE 7

5-[3-[[(2,3-Dihydro-1,4-benzodioxin-2-yl)methyl]amino]propoxyl-2(1H)-quinolinone 2,3-Dihydro-1,4-benzodioxin-2-methanamine (0.56 g, 4.0 mmole), 5-(3-chloropropoxy)carbostyril (0.70 g, 3.1 mmole), diisopropylethylamine (0.65 g, 5.0 mmole) and sodium iodide (1.0 g, 6.5 mmole) were combined in 50 ml of DMF and heated at 80° C. for 24 hours under a nitrogen atmosphere. The solvent was then removed and replaced with 250 ml of dichloromethane. The mixture was washed with an equal volume of saturated aqueous sodium bicarbonate, with saturated aqueous sodium chloride, dried over sodium sulfate, filtered, and concentrated in vacuum. The residue was column chromatographed on 50 g of silica gel with a gradient elution commencing with chloroform and ending with 2% methanol in chloroform. The product-containing fractions were combined and concentrated in vacuum and the residue crystallized from isopropanol with the addition of 4N isopropanolic HCl to give 125 mg of title compound as a tan solid, monohydrochloride, quarter hydrate, m.p. 242°-244° C.

Elemental Analysis for: $C_{21}H_{22}N_2O_4 \cdot HCl \cdot \frac{1}{4}H_2O$: Calcd: C, 61.91; H, 5.81; N, 6.88; Found: C, 61.94; H, 5.90; N, 6.80

EXAMPLE 8

(S)-7-[3-[[(2,3-Dihydro-6-hydroxy-1,4-benzodioxin-2-yl)methyl]amino]propoxy]-2H-1-benzopyran-2-one (S)-2,3-Dihydro-6-hydroxy-1,4-benzodioxin-2-methanamine (2.89 g, 16.0 mmole), 7-(3-chloropropoxy)coumarin (3.46 g, 14.5 mmole), diisopropylethylamine (12.5 ml, 72 mmole) and sodium iodide (2.20 g, 14.7 mmole) were combined in 200 ml of DMF and heated at 80°-100° C. for 24 hours under a nitrogen atmosphere. The solvent was then removed in vacuum. The residue was column chromatographed on silica gel using first 0.5% methanol/dichloromethane, then 1% methanol/dichloromethane, and finally 3% methanol/dichloromethane as eluant. The product-containing fractions (Rf=0.45 on silica gel with 5% methanol/dichloromethane) were combined and rechromatographed on silica gel using first 75% ethyl acetate/dichloromethane and then 2% methanol/dichloromethane as eluant. The product-containing fractions were concentrated in vacuum and the pure free base (0.98 g) redissolved in methanol and boiled on a hot plate, the methanol gradually being replaced with isopropanol. 4N HCl/isopropanol (7.0 ml) was added and the title compound was collected by filtration and dried in vacuum at 80° C. The procedure yielded 0.71 g of white solid, monohydrochloride, m.p. 236°–239° C.

Elemental Analysis for: $C_{21}H_{21}NO_6 \cdot HCl$: Calcd: C, 60.07; H, 5.28; N, 3.34; Found: C, 59.95; H, 5.26; N, 3.53

EXAMPLE 9

7-[3-[[(2,3-Dihydro-7-methoxy-1,4-benzodioxin-2-yl)methyl]amino]propoxy]-2H-1-benzopyran-2-one 2,3-Dihydro-7-methoxy-1,4-benzodioxin-2-methanamine (3.8 g, 20 mmole), 7-(3-chloropropoxy)coumarin (4.8 g, 20 mmole), diisopropylethylamine (2.6 g, 20 mmole) and sodium iodide (5.0 g, 33 mmole) were combined in 200 ml of DMF and heated at 100° C. for 24 hours under a nitrogen atmosphere. The solvent was then removed and replaced with 500 ml of dichloromethane. The mixture was washed with 300 ml portions of saturated aqueous sodium bicarbonate, with saturated aqueous sodium chloride, dried over sodium sulfate, filtered, and concentrated in vacuum. The residue was column chromatographed on 100 g of silica gel using first dichloromethane, then chloroform, and finally 2% methanol in chloroform as eluant. The product-containing fractions were combined and concentrated in vacuum and the residue crystallized from 100 ml of isopropanol with the addition of 5.0 ml of 4N isopropanolic HCl to give 3.2 g of title compound as a white solid, monohydrochloride, m.p. 223°–225° C.

Elemental Analysis for: $C_{22}H_{23}NO_6 \cdot HCl$: Calcd: C, 60.90; H, 5.58; N, 3.23; Found: C, 61.09; H, 5.42; N, 3.32

EXAMPLE 10

(R)-7-[3-[[(2,3-Dihydro-6-hydroxy-1,4-benzodioxin-2-yl)methyl]amino]propoxy]-2H-1-benzopyran-2-one (R)-2,3-Dihydro-6-hydroxy-1,4-benzodioxin-2-methanamine (2.58 g, 14.2 mmole), 7-(3-chloropropoxy)coumarin (3.08 g, 12.9 mmole), diisopropylethylamine (10 ml, 57 mmole) and sodium iodide (1.98 g, 13.2 mmole) were combined in 175 ml of DMF and heated at 94° C. for 24 hours under a nitrogen atmosphere. The solvent was then removed in vacuum. The residue was twice column chromatographed on silica gel using 1% methanol/dichloromethane as eluant. The product-containing fractions (Rf=0.45 on silica gel with 5% methanol/dichloromethane) were combined and concentrated in vacuum and the pure free base redissolved in methanol and boiled on a hot plate, the methanol gradually being replaced with isopropanol. 4N HCL/isopropanol was added and the title compound was collected by filtration. After two additional recrystallizations from isopropanol, 0.35 g of white solid, monohydrochloride, m.p. 236°–242° C., was obtained.

Elemental Analysis for: $C_{21}H_{21}NO_6 \cdot HCl$: Calcd: C, 60.07; H, 5.28; N, 3.34; Found: C, 60.12; H, 5.20; N, 3.26

EXAMPLE 11

7-[3-[[(2,3-Dihydro-6-acetoxy-1,4-benzodioxin-2-yl)methyl]amino]propoxy]-2H-1-benzopyran-2-one 7-[3-[[(2,3-Dihydro-6-hydroxy-1,4-benzodioxin-2-yl)methyl]amino]propoxy]-2H-1-benzopyran-2-one hydrochloride (0.10 g, 0.24 mmole), prepared as in example 5 above, was dissolved in 50 ml of glacial acetic acid and 3.05 ml (43 mmole) of acetyl chloride added in portions over a 30 minute period, during which the reaction mixture was gently warmed with a heat gun. The solvent and excess reagent were then removed in vacuum and diethyl ether added. Upon standing overnight, 0.030 g of the title compound as a monohydrochloride, m.p. 175° C., crystallized.

Elemental Analysis for: $C_{23}H_{23}NO_7 \cdot HCl$: Calcd: C, 59.81; H, 5.24; N, 3.03; Found: C, 59.42; H, 5.39; N, 2.98

EXAMPLE 12

7-[3-[[(2,3-Dihydro-7-hydroxy-1,4-benzodioxin-2-yl)methyl]ethylamino]propoxy]-2H-1-benzopyran-2-one N-Ethyl-2,3-dihydro-7-hydroxy-1,4-benzodioxin-2-methanamine (2.11 g, 13.1 mmole), 7-(3-chloropropoxy)coumarin (3.44 g, 14.4 mmole), diisopropylethylamine (11 ml, 63.2 mmole) and sodium iodide (1.98 g, 13.2 mmole) were combined in 175 ml of DMF and heated at 94° C. for 2 days under a nitrogen atmosphere. The solvent was then removed in vacuum and the residue column chromatographed on silica gel using first 0.5% methanol/dichloromethane and then 1.5% methanol/dichloromethane as eluant. The product-containing fractions were combined and concentrated in vacuum and the residue redissolved in dichloromethane and boiled on a hot plate, the dichloromethane gradually being replaced with isopropanol. 4N HCl/isopropanol (4 ml) was added and the title compound was collected by filtration. A second recrystallization from isopropanol yielded 0.73 g of white solid, monohydrochloride, m.p. 208°–215° C.

Elemental Analysis for: $C_{23}H_{25}NO_6 \cdot HCl$: Calcd: C, 61.68; H, 5.85; N, 3.13; Found: C, 61.71; H, 5.97; N, 2.96

EXAMPLE 13

7-[3-[[(2.3-Dihydro-7-chloro-1,4-benzodioxin-2-yl)methyl]amino]propoxy]-2H-1-benzopyran-2-one 2,3-Dihydro-7-chloro-1,4-benzodioxin-2-methanamine (1.72 g, 8.62 mmole), 7-(3-chloropropoxy)coumarin (1.88 g, 7.88 mmole), diisopropylethylamine (7.5 ml, 43.1 mmole) and sodium iodide (1.37 g, 9.14 mmole) were combined in 200 ml of DMF and heated at 80°–100° C. for 3 days under a nitrogen atmosphere. The solvent was then removed in vacuum and the residue was column chromatographed on silica gel using first 0.5% methanol/dichloromethane and then 1% methanol/dichloromethane as eluant. The product-containing fractions were combined and concentrated in vacuum, during which procedure the free base began to come out of solution. This material was collected by filtration and recrystallized from isopropanol with addition of 4N HCl/isopropanol to give 0.27 g of white solid, monohydrochloride, m.p. 235°–242° C.

Elemental Analysis for: $C_{21}H_{20}ClNO_5 \cdot HCl$: Calcd: C, 57.55; H, 4.83; N, 3.20; Found: C, 57.19; H, 4.86; N, 3.07

EXAMPLE 14

7-[3-[[(2.3-Dihydro-7-methoxy-1,4-benzodioxin-2-yl)methyl]methylamino]propoxy]-2H-1-benzopyran-2-one 7-[3-[[(2,3-Dihydro-7-methoxy-1,4-benzodioxin-2-yl)methyl]amino]propoxy]-2H-1-benzopyran-2-one hydrochloride (2.2 g, 5.0 mmole) was dissolved in 100 ml of DMF and 700 mg (5.0 mmole) of methyl iodide added, followed by 2.6 g (20 mmole) of diisopropylethylamine. The mixture was heated at 80° C. for 24 hours under a nitrogen atmosphere. The solvent was then removed in vacuum and replaced with 300 ml of dichloromethane. The mixture was washed with 300 ml portions of saturated aqueous sodium bicarbonate, saturated sodium chloride solution, dried over sodium sulfate, filtered and concentrated in vacuum. The residue was purified by column chromatography on 100 g of silica gel using chloroform as eluant and crystallized from isopropanol with addition of 2.5 ml of 4N isopropanolic HCl to give 0.20 g of the title compound as a monohydrochloride, m.p. 176°–178° C.

Elemental Analysis for: $C_{23}H_{25}NO_6 \cdot HCl$: Calcd: C, 61.67; H, 5.85; N, 3.13; Found: C, 61.71; H, 5.62; N, 3.25

EXAMPLE 15

7-[3-[[(2.3-Dihydro-6-hydroxy-1,4-benzodioxin-2-yl)methyl]methylamino]propoxy]-2H-1-benzopyran-2-one N-Methyl-2,3-dihydro-6-hydroxy-1,4-benzodioxin-2-methanamine (3.68 g, 17.3 mmole), 7-(3-chloropropoxy)coumarin (4.15 g, 17.4 mmole), diisopropylethylamine (4.4 ml, 25.3 mmole) and sodium iodide (2.59 g, 17.3 mmole) were combined in 75 ml of DMF and heated at 96° C. for 26 hours under a nitrogen atmosphere. The solvent was then removed in vacuum and the residue was column chromatographed on silica gel using first 1% methanol/dichloromethane, then 2% methanol/dichloromethane as eluant. The product-containing fractions were combined and concentrated in vacuum and the residue crystallized from isopropanol with addition of 4N HCl/isopropanol and diethyl ether to give 1.71 g of white solid, monohydrochloride, quarter hydrate, m.p. 186°–193° C.

Elemental Analysis for: $C_{22}H_{23}NO_6 \cdot HCl \cdot \frac{1}{4}H_2O$: Calcd: C, 60.28; H, 5.63; N, 3.19; Found: C, 60.21; H, 5.59; N, 3.17

EXAMPLE 16

(S)-7-[3-[[(2,3-Dihydro-6,7-methylenedioxy-1,4-benzodioxin-2-yl)methyl]amino]propoxy]-2H-1-benzopyran-2-one (S)-2,3-Dihydro-6,7-methylenedioxy-1,4-benzodioxin-2-methanamine hydrochloride (5.50 g, 22.4 mmole), 7-(3-chloropropoxy)coumarin (5.49 g, 23.0 mmole) diisopropylethylamine (39.0 ml, 224 mmol) and sodium iodide (3.45 g, 23.0 mmole) were combined in 200 ml of DMF and heated at 80° C. for 24 hours under a nitrogen atmosphere. The solvent was then removed in vacuum and replaced with chloroform. The mixture was treated with an equal volume of saturated aqueous sodium bicarbonate and the aqueous phase was then back-extracted with 3:1 chloroform-isopropanol. The combined organic extracts were washed with water, dried over anhydrous magnesium sulfate, filtered and concentrated under vacuum. The residue was chromatographed on a silica gel column using dichloromethane as eluant. The product-containing fractions (Rf=0.59 on silica gel tlc with 1:5:95 ammonium hydroxide-methanol-chloroform) were combined and concentrated in vacuum, and the residue redissolved in methanol and acidified with 4N HCl/isopropanol to pH<3 in an ice bath to precipitate a white solid. This was recrystallized from methanol and triturated with a small amount of isopropanol to give 1.50 g of the title compound as an off-white crystalline, solid, monohydrochloride, m.p. 244°–245° C.

Elemental Analysis for: $C_{22}H_{21}NO_7 \cdot HCl$: Calcd: C, 59.00; H, 4.95; N, 3.13; Found: C, 59.07; H, 4.92; N, 2.94

EXAMPLE 17

(S)-7-[3-[[(2,3-Dihydro-6,7-methylenedioxy-1,4-benzodioxin-2-yl)methyl]ethylamino]propoxy]-2H-1-benzopyran-2-one (S)-7-[3-[[(2,3-Dihydro-6,7-methylenedioxy-1,4-benzodioxin-2-yl)methyl]amino]propoxy]-2H-1-benzopyran-2-one hydrochloride (0.60 g, 1.3 mmole), iodoethane (0.16 ml, 2.0 mmole) and diisopropylethylamine (2.26 ml, 13.0 mmole) were combined in 50 ml of DMF and heated at 60° C. for 2 days under a nitrogen atmosphere. The solvent was then removed in vacuum and the residue was dissolved in dichloromethane and washed with an equal volume of aqueous saturated sodium bicarbonate. The aqueous portion was back-extracted with dichloromethane and the combined organic portions were washed with water, dried over anhydrous magnesium sulfate, filtered, and concentrated under reduced pressure. The residue was chromatographed on a silica gel column using dichloromethane as eluant. The product-containing fractions were combined and concentrated in vacuum, and the residue redissolved in methanol and acidified with 4N HCl/isopropanol to pH<3 in an ice bath. The mixture was diluted with isopropanol to precipitate a white solid, which was recrystallized from methanol to give 0.25 g of the title compound as the monohydrochloride, m.p. 209° C.

Elemental Analysis for: $C_{24}H_{25}NO_7 \cdot HCl$: Calcd: C, 60.57; H, 5.51; N, 2.94; Found: C, 60.44; H, 5.27; N, 2.91

EXAMPLE 18

(S)-7-[3-[[(2,3-Dihydro-7-methoxy-1,4-benzodioxin-2-yl)methyl]amino]propoxy]-2H-1-benzopyran-2-one (S)-2,3-Dihydro-7-methoxy-1,4-benzodioxin-2-methanamine hydrochloride (11.5 g, 49.8 mmole), 7-(3-bromopropoxy)coumarin (14.2 g, 50.0 mmole), and diisopropylethylamine (12 ml, 68.9 mmole) were combined in 350 ml of DMF and heated at 90° C. for 24 hours uunder a nitrogen atmosphere. The solvent was then removed in vacuum and replaced with 300 ml of dichloromethane. Upon addition of an equal volume of saturated aqueous sodium bicarbonate, a white solid precipitated. This was filtered and redissolved in 550 ml of warm methanol and 35 ml of 4N isopropanolic HCl was added. The solution was boiled on a hot plate and the solvent gradually replaced with isopropanol. Upon cooling, 0.54 g of the title compound precipitated as a white solid, monohydrochloride, quarter hydrate, m.p. 225°–227° C. Subsequent crops yielded as additional 6.1 g of product.

Elemental Analysis for: $C_{22}H_{23}NO_6 \cdot HCl \cdot \frac{1}{4}H_2O$: Calcd: C, 60.27; H, 5.57; N, 3.19; Found: C, 59.98; H, 5.45; N, 3.04

EXAMPLE 19

7-[3-[[(2,3-Dihydro-6,8-dimethoxy-1,4-benzodioxin-2-yl)methyl]amino]propoxy]-2H-1-benzopyran-2-one 2,3-Dihydro-6,8-dimethoxy-1,4-benzodioxin-2-methanamine hydrochloride (3.58 g, 13.7 mmole), 7-(3-bromopropoxy)coumarin (3.35 g, 11.8 mmole), and diisopropylethylamine (3.25 ml, 18.7 mmole) were combined in 200 ml of DMF and heated at 96° C. for 2 days under a nitrogen atmosphere. The solvent was then removed and replaced with dichloromethane. The mixture was washed with an equal volume of saturated aqueous sodium bicarbonate, dried over magnesium sulfate, filtered and concentrated in vacuum. The residue was column chromatographed on 300 g of silica gel using first dichloromethane and then 1% methanol/dichloromethane as eluant. The product-containing fractions were combined and concentrated in vacuum and the free base thus obtained redissolved in methanol and 7 ml of 4N isopropanolic HCl added. The mixture was brought to a boil on a hot plate and the solvent gradually replaced with isopropanol. Upon cooling, 0.87 g of the title compound (m.p. 184°-187° C.) precipitated as a white solid, monohydrochloride.

Elemental Analysis for: $C_{23}H_{26}ClNO_7 \cdot HCl$: Calcd: C, 59.55; H, 5.65; N, 3.02; Found: C, 59.22; H, 5.63; N, 3.08

EXAMPLE 20

(S)-7-[3-[[(2,3-Dihydro-7-hydroxy-1,4-benzodioxin-2-yl)methyl]amino]propoxy]-2H-1-benzopyran-2-one (S)-2,3-Dihydro-7-hydroxy-1,4-benzodioxin-2-methanamine (3.53 g, 16.2 mmole), 7-(3-bromopropoxy)coumarin (4.17 g, 14.7 mmole), and diisopropylethylamine (5.00 ml, 28.7 mmole) were combined in 300 ml of DMF and heated at 86° C. for 24 hours under a nitrogen atmosphere. The solvent was then removed in vacuum and replaced with dichloromethane. The mixture was washed with an equal volume of saturated aqueous sodium bicarbonate, dried over magnesium sulfate, filtered and concentrated in vacuum. The residue was column chromatographed on 300 g of silica gel using first 75% ethyl acetate/dichloromethane and then 2% methanol/dichloromethane as eluant. The product-containing fractions were concentrated in vacuum and the free base redissolved in warm methanol. Five ml of 4N isopropanolic HCl was added, the mixture was brought to a boil on a hot plate and the solvent gradually replaced with isopropanol. Upon cooling, 2.24 g of the title compound precipitated as an white solid, monohydrochloride, m.p. 245°-248° C.

Elemental Analysis for: $C_{21}H_{21}NO_6 \cdot HCl$: Calcd: C, 60.07; H, 5.28; N, 3.34; Found: C, 59.92; H, 5.31; N, 3.31

EXAMPLE 21

(S)-7-[3-[[(2,3-Dihydro-7-hydroxy-1,4-benzodioxin-2-yl)methyl]ethylamino]propoxy]-2H-1-benzopyran-2-one (S)-7-[3-[[(2,3-Dihydro-7-hydroxy-1,4-benzodioxin-2-yl)methyl]amino]propoxy]-2H-1-benzopyran-2-one hydrochloride (0.89 g, 2.13 mmole), diisopropylethylamine (0.80 ml, 4.59 mmole) and iodoethane (0.24 ml, 3.0 mmole) were combined in DMF and heated at 60° C. for 15 hours under a nitrogen atmosphere. The solvent was then removed in vacuum and replaced with 75 ml of dichloromethane. The mixture was washed with an equal volume of saturated aqueous sodium bicarbonate, dried over magnesium sulfate, filtered and concentrated in vacuum. The residue (1.82 g) was column chromatographed on 75 g of silica gel using first 0.5% methanol/dichloromethane and then 2% methanol/dichloromethane as eluant. The product-containing fractions were concentrated in vacuum and the free base redissolved in methanol. 2.8 ml of 4N isopropanolic HCl was added, the mixture was brought to a boil on a hot plate and the solvent gradually replaced with isopropanol. Upon cooling, 0.66 g of the title compound precipitated as a yellow solid, monohydrochloride, quarter hydrate, m.p. 204°-207° C.

Elemental Analysis for: $C_{23}H_{25}NO_6 \cdot HCl \cdot \frac{1}{4}H_2O$: Calcd: C, 61.06; H, 5.90; N, 3.09; Found: C, 61.22; H, 5.75; N, 2.93

EXAMPLE 22

7-[3-[[(2,3-Dihydro-1,4-benzodioxin-2-yl)methyl]ethylamino]propoxyl-2H-1-benzopyran-2-one N-Ethyl-2,3-dihydro-1,4-benzodioxin-2-methanamine (4.67 g, 24.2 mmole), 7-(3-bromopropoxy)coumarin (6.92 g, 24.4 mmole), and diisopropylethylamine (6.70 ml, 38.5 mmole) were combined in 300 ml of DMF and heated at 76° C. for 24 hours under a nitrogen atmosphere. The solvent was then removed in vacuum and replaced with dichloromethane. The mixture was washed with an equal volume of saturated aqueous sodium bicarbonate, dried over magnesium sulfate, filtered and concentrated in vacuum. The residue (10 g) was column chromatographed on 225 g of silica gel using 40% ethyl acetate/dichloromethane as eluant. The product-containing fractions were concentrated in vacuum and the residue crystallized from isopropanol with the addition of 30 ml of 4N isopropanolic HCl to give 4.94 g of the title compound as a white solid, monohydrochloride, m.p. 147°-152° C.

Elemental Analysis for: $C_{23}H_{25}NO_5 \cdot HCl$: Calcd: C, 63.95; H, 6.07; N, 3.24; Found: C, 63.74; H, 5.91; N, 3.06

What is claimed is:

1. A compound of the formula:

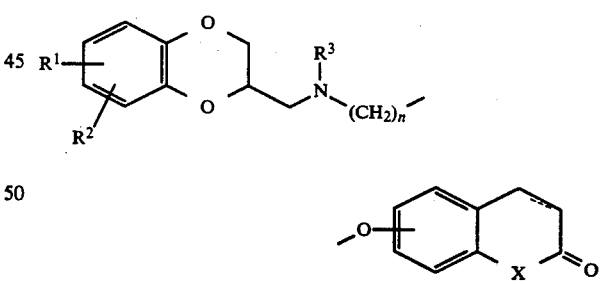

wherein
the dotted line represents optional unsaturation;
$R^1$ and $R^2$ are, independently, hydrogen, alkyl of 1 to 6 carbon atoms, alkoxy of 1 to 6 carbon atoms, aralkoxy of 7 to 12 carbon atoms, alkanoyloxy of 2 to 6 carbon atoms, hydroxy, halo, amino, mono- or dialkylamino in which each alkyl group has 1 to 6 carbon atoms, alkanamido of 2 to 6 carbon atoms or sulfonamido or $R^1$ and $R^2$ together are methylenedioxy, ethylenedioxy or propylenedioxy;
$R^3$ is hydrogen or alkyl of 1 to 6 carbon atoms;
n is one of the integers 2, 3 or 4;
X is O;
or a pharmaceutically acceptable salt thereof.

2. A compound of claim 1 in which R¹ and R² are, independently, hydrogen, fluoro, hydroxy, alkoxy of 1 to 6 carbon atoms, alkanoyloxy of 2 to 6 carbon atoms, or, taken together, R¹ and R² are methylenedioxy, ethylenedioxy or propylenedioxy and the —(CH$_2$)$_n$—O— link is to the 7-position of the coumarin nucleus, or a pharmaceutically acceptable salt thereof.

3. A compound of claim 1 of the formula:

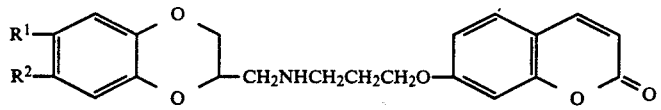

in which R¹ and R² are, independently, hydrogen, fluoro, hydroxy, alkoxy of 1 to 6 carbon atoms, alkanoyloxy of 2 to 6 carbon atoms, or, taken together, R¹ and R² are methylenedioxy, ethylenedioxy or propylenedioxy, or a pharmaceutically acceptable salt thereof, wherein the benzodioxan methanamine moiety is in the S-configuration.

4. The compound of claim 1 which is 7-[3-[[(2,3-dihydro-1,4-benzodioxin-2-yl)methyl]amino]propoxy]-2H-1-benzopyran-2-one, or a pharmaceutically acceptable salt thereof.

5. The compound of claim 1 which is 7-[3-[[(2,3-dihydro-5-methoxy-1,4-benzodioxin-2-yl)methyl]amino]propoxy]-2H-1-benzopyran-2-one, or a pharmaceutically acceptable salt thereof.

6. The compound of claim 1 which is 7-[3-[[(2,3-dihydro-7-phenylmethoxy-1,4-benzodioxin-2-yl)methyl]amino]propoxy]-2H-1-benzopyran-2-one, or a pharmaceutically acceptable salt thereof.

7. The compound of claim 1 which is 7-[3-[[(2,3-dihydro-6-phenylmethoxy-1,4-benzodioxin-2-yl)methyl]amino]propoxy]-2H-1-benzopyran-2-one, or a pharmaceutically acceptable salt thereof.

8. The compound of claim 1 which is 7-[3-[[(2,3-dihydro-6-hydroxy-1,4-benzodioxin-2-yl)methyl]amino]propoxy]-2H-1-benzopyran-2-one, or a pharmaceutically acceptable salt thereof.

9. The compound of claim 1 which is 7-[3-[[(2,3-dihydro-7-hydroxy-1,4-benzodioxin-2-yl)methyl]amino]propoxy]-2H-1-benzopyran-2-one, or a pharmaceutically acceptable salt thereof.

10. The compound of claim 1 which is 7-[3-[[(2,3-dihydro-7-methoxy-1,4-benzodioxin-2-yl)methyl]amino]propoxy]-2H-1-benzopyran-2-one, or a pharmaceutically acceptable salt thereof.

11. The compound of claim 1 which is 7-[3-[[(2,3-dihydro-6-acetoxy-1,4-benzodioxin-2-yl)methyl]amino]propoxy]-2H-1-benzopyran-2-one, or a pharmaceutically acceptable salt thereof.

12. The compound of claim 1 which is 7-[3-[[(2,3-dihydro-7-hydroxy-1,4-benzodioxin-2-yl)methyl]ethylamino]propoxy]-2H-1-benzopyran-2-one, or a pharmaceutically acceptable salt thereof.

13. The compound of claim 1 which is 7-[3-[[(2,3-dihydro-7-chloro-1,4-benzodioxin-2-yl)methyl]amino]propoxy]-2H-1-benzopyran-2-one, or a pharmaceutically acceptable salt thereof.

14. The compound of claim 1 which is 7-[3-[[(2,3-dihydro-7-methoxy-1,4-benzodioxin-2-yl)methyl]methylamino]propoxy]-2H-1-benzopyran-2-one, or a pharmaceutically acceptable salt thereof.

15. The compound of claim 1 which is 7-[3-[[(2,3-dihydro-6-hydroxy-1,4-benzodioxin-2-yl)methyl]methylamino]propoxy]-2H-1-benzopyran-2-one, or a pharmaceutically acceptable salt thereof.

16. The compound of claim 1 which is 7-[3-[[(2,3-dihydro-6,8-dimethoxy-1,4-benzodioxin-2-yl)methyl]amino]propoxy]-2H-1-benzopyran-2-one, or a pharmaceutically acceptable salt thereof.

17. The compound of claim 1 which is 7-[3-[[(2,3-dihydro-1,4-benzodioxin-2-yl)methyl]ethylamino]proproxy]-2H-1-benzopyran-2-one, or a pharmaceutically acceptable salt thereof.

* * * * *